United States Patent
Breker et al.

(10) Patent No.: US 6,428,778 B1
(45) Date of Patent: Aug. 6, 2002

(54) PROCESS FOR THE SYNTHESIS OF FINELY DIVIDED ANTIPERSPIRANT ACTIVE INGREDIENT SUSPENSIONS

(75) Inventors: Johannes Breker, Ludwigshafen; Bruno Kaufmann, Frankenthal; Wolfgang Reibel, Ludwigshafen; Klaus Schanz, Dannstadt, all of (DE)

(73) Assignee: BK Guilini Chemie GmbH und Co OHG, Ludwigshafen (DE)

( * ) Notice: Subject to any disclaimer, the term of this patent is extended or adjusted under 35 U.S.C. 154(b) by 0 days.

(21) Appl. No.: 09/578,731

(22) Filed: May 26, 2000

(30) Foreign Application Priority Data

May 29, 1999 (EP) .............................. 99110457

(51) Int. Cl.$^7$ ............................ A61K 7/38; A61K 7/32; A61K 33/06; A01N 59/06
(52) U.S. Cl. .................... 424/68; 423/111; 423/462; 423/463; 423/465; 424/65; 424/401; 424/682; 424/685
(58) Field of Search ............................ 424/401, 65, 68, 424/682, 685; 423/462, 463, 465, 111

(56) References Cited

U.S. PATENT DOCUMENTS

| 4,018,888 | A | * | 4/1977 | Scripps et al. ................ 424/47 |
| 4,359,456 | A | | 11/1982 | Gosling et al. ................ 424/68 |
| 5,417,964 | A | * | 5/1995 | Carlson, Sr. et al. ......... 424/66 |
| 5,444,096 | A | * | 8/1995 | McCrea et al. ............. 514/770 |
| 5,955,065 | A | * | 9/1999 | Thong et al. ................ 424/68 |
| 6,136,302 | A | * | 10/2000 | Juneja et al. ................ 424/65 |

FOREIGN PATENT DOCUMENTS

| GB | 2 048 229 A | 12/1980 |

* cited by examiner

Primary Examiner—Jose' G. Dees
Assistant Examiner—Marina Lamm
(74) Attorney, Agent, or Firm—Venable; George H. Spencer; Ashley J. Wells

(57) ABSTRACT

A process for synthesis of finely divided antiperspirant suspensions includes providing an antiperspirant salt consisting essentially of an Al salt which is effective as an antiperspirant and which is described by an empirical formula as follows: $Al(OH)_{(3-b)}X_b zH_2O$ where b=0.4 to 3, z<4, and X=halogen; mixing the Al salt into a non-aqueous oil phase to provide a mixture; and subsequently grinding the mixture with a suitable milling device at a temperature below 80° C. to provide a suspension having a preselected fineness. A perspiration-inhibiting cosmetic preparation includes, as active ingredient, the antiperspirant suspension described above.

14 Claims, No Drawings

PROCESS FOR THE SYNTHESIS OF FINELY DIVIDED ANTIPERSPIRANT ACTIVE INGREDIENT SUSPENSIONS

BACKGROUND OF THE INVENTION

1. Field of the Invention

The subject of the present invention is a process for the manufacture of suspensions containing finely divided basic aluminium halide, which produce good sweat reduction on human skin and are also simple to utilise.

2. Description of the Related Art

The prior art already includes a series of processes for the synthesis of aluminium hydroxyhalide complexes that can be used as antiperspirant active ingredients. Although the patents usually encompass the entire range of halides and other monovalent non-coordinating anions, only the chlorides have acquired a practical significance.

Apart from the standard processes for the manufacture of the simple ca. 50% aqueous aluminium chlorohydrate solutions by dissolving Al metal in a hypostoichiometric quantity of hydrochloric acid, processes for the synthesis of so-called activated aluminium chlorohydrates also exist.

For the manufacture of activated aluminium chlorohydrates, Gosling et al. (U.S. Pat. No. 4,359,456) start with standard aluminium chlorohydrate solutions and, after dilution at temperatures in the range between 50° and 140° C., perform tempering. This tempering leads to a change in the polymer species distribution. The higher molecular proportions of the standard aluminium chlorohydrate are broken down in favour of smaller species, so that the solution no longer contains species of larger than 100 Å. Analytical characterisation of the aluminium chlorohydrate complexes made in this way was carried out with the aid of size-exclusion chromatography. Using this method, the proportion of low molecular complexes, and therefore the activation level, can be followed.

It has been found that the aluminium chlorohydrate complexes were particularly effective as antiperspirants if they contained high proportions of Band III (relative retention time ca. 0.79).

A similar synthesis concept was pursued by Fitzgerald et al. (UK-2 048 229) by ageing 10–25% aluminium chlorohydrate solutions at 50° C. to 80° C. for between 8 hours and 3 weeks.

According to both alternative processes, the species distribution produced by the activation conditions is not stable in aqueous solution, so that only through protective drying can an effective antiperspirant active ingredient that is stable in storage be obtained. The patents describe spray drying as the preferred drying method.

In antiperspirant finished formulations, currently either sieve fractions of the spray-dried powder (e.g. aerosols) or fine powders obtained by dry milling (roll-ons or sticks) are used.

It has thus not been possible previously to produce a stable effective aluminium antiperspirant active ingredient in liquid form. The processing of powder-form active ingredients, however always presents great problems for the formulator. Furthermore, due to the low pH value of the (humid) powder, the health of workers involved with it is endangered.

There was therefore a need for better, more easily handled antiperspirant active ingredients, without sacrificing the greater effectiveness of previous powder products. Furthermore, it was not possible to fulfill all the formulation wishes of the cosmetics industry with the powder-form aluminium chlorohydrate complexes available. For instance, the manufacture of certain semisolid formulations—so-called soft solids—proved to be extremely difficult.

SUMMARY OF THE INVENTION

It was then unexpectedly discovered that particularly easily handled and simultaneously effective aluminium hydroxyhalide-containing antiperspirant active ingredient suspensions were obtained when the active ingredient fulfilling the following formula and conditions $$Al(OH)_{(3-b)}X_b zH_2O$$

where
b=0.4 to 3, particularly b=0.45 to 1.0
z<4
X=halogen, particularly chlorine
whereby the HPLC chromatogram of the active ingredient has a band III share of >30%, particularly >40%, and optionally a buffer substance, is mixed into a non-aqueous oil phase while excluding humidity, and subsequently ground at temperatures below 60° C. to the required fineness with a grinding device.

As a result of the direct wet grinding of the spray product, the laborious and dust-generating powder sieving and dry grinding is dispensed with, and suspensions are obtained that are more stable than those that can be obtained by suspension of dry-ground powder.

These antiperspirant active ingredients are non-aqueous suspensions characterised in that the non-aqueous phase consists of a substantially non-polar non-water-miscible organic liquid of the substance groups alkanes, isoalkanes, monofunctional alcohols, polyfunctional alcohols, fatty acid esters of monobasic and dibasic carboxylic acids with monofunctional and polyfunctional alcohols, polyoxyethylenes, polyoxypropylenes, polyalkoxylate ethers of alcohols, cyclic silicones, open-chain silicones and combinations of these. In particular, the non-aqueous oil phase consists of silicone oil.

According to the invention, silicone oil components used are cyclic silicones, open-chain silicones or mixtures of these. They can be used as mixtures with other cosmetically acceptable oils.

The finely divided antiperspirant suspensions according to the invention can contain the amino acids glycine and/or alanine as buffer substances.

The process for the manufacture of finely divided antiperspirant suspensions is characterised in that an aluminium salt effective as an antiperspirant may possibly be mixed in the presence of the amino acid, preferably glycine, with exclusion of humidity in a non-aqueous oil phase and then ground. A ball mill is preferably used as the grinding device.

An aluminium salt that is used and is effective as an antiperspirant, is a basic aluminium halide of the following composition:

$$Al(OH)_{(3-b)}X_b zH_2O$$

where
b=0.4 to 3, particularly b=0.45 to 1.0
z<4
X=halogen, especially chlorine
where the HPLC chromatogram of the active ingredient preferably has a band III proportion of >30%, and particularly >40%.

In the case of the variant containing one amino acid, a basic aluminium halide of the following composition is used as an aluminium salt effective as an antiperspirant:

Al(OH)$_{(3-b)}$X$_b$ (amino acid) $z$H$_2$O where

X=halogen, especially chlorine b=0.4 to 3, particularly b=0.45 to 1.0 z<2 and the molar ratio of amino acid to aluminium is between 0 and 0.33.

The grinding of the antiperspirant suspension in the process according to the invention is characterised in that this procedure is carried out at temperatures below 60° C., and particularly at below 40° C. The antiperspirant suspensions are advantageously applied in non-aqueous formulations, e.g. in aerosols, sticks and so-called soft solids. The following examples serve to illustrate the invention:

DESCRIPTION OF THE PREFERRED EMBODIMENTS

EXAMPLES OF SUSPENSIONS ACCORDING TO THE INVENTION

Example 1

130 kg cyclomethicone (DC 345 from Dow-Corning) is placed in a 400 l reactor with a propeller stirrer. While stirring, 159 kg of activated aluminium chlorohydrate powder with an aluminium content of 26.0% and a chlorine content of 17.0%, synthesised according to the U.S. Pat. No. 4,359,456, is mixed in. The homogeneous suspension with a solid content of 55% was then very finely ground with a ball mill to a final fineness of 99.9%<12 µm and 90%<9 µm. The starting temperature of the product suspension was 25°–30° C. The resulting thixotropic suspension capable of being pumped is stable with regard to sedimentation.

Example 2

(according to the invention)

22.5 kg cyclomethicone (DC 345 from Dow-Corning) is placed in a 100 l reactor with a propeller stirrer. While stirring, 22.46 kg of activated aluminium chlorohydrate powder with an aluminium content of 26% and a chlorine content of 17.1%, synthesised according to the U.S. Pat. No. 4,359,456, and 5.04 kg glycine is added.

The homogeneous suspension with a solid content of 55% was then very finely ground in a ball mill (from Fryma—CoBall-Mill) to a final fineness of 99%<18 µm and 90%<9 µm. The starting temperature of the product suspension was 25°–30° C. The resulting thixotropic suspension capable of being pumped is stable with regard to sedimentation.

Example 3

20 kg cyclomethicone (DC 345 from Dow-Corning) is placed in a 100 l reactor with a propeller stirrer. While stirring, 30 kg of activated aluminium chlorohydrate powder with an aluminium content of 26% and a chlorine content of 17.1%, synthesised according to the U.S. Pat. No. 4,359,456, is added.

The homogeneous suspension with a solid content of 60% was then ground with a ball mill (from Fryma—CoBall-Mill) to a final fineness of 99%<71 µm. The starting temperature of the product suspension was 25°–30° C. The resulting thixotropic suspension capable of being pumped is stable with regard to sedimentation.

Comparison Example 2220 g cyclomethicone (DC 345 from Dow-Corning) is placed in a 10 l container with a propeller stirrer. While stirring, 2750 g of activated aluminium chlorohydrate powder with an aluminium content of 26% and a chlorine content of 17%, synthesised according to the U.S. Pat. No. 4,359,456, ground with an air-jet mill to a fineness of 99%<10 µm, was added. The homogeneous suspension with a solid content of 55% was highly fluid and not stable with regard to sedimentation.

The following gives an overview, without imposing limitations, of usage of the suspensions according to the invention in cosmetic formulations:

| | | | A | B |
|---|---|---|---|---|
| | | | \multicolumn{2}{c}{Roll-on formulations} | |
| | Components | INCI designation | \multicolumn{2}{c}{Proportion by weight (%)} |
| 1a | Sample as Example 2 | Aluminium chlorohydrate, cyclomethicone pentamer | 40 | — |
| 1b | Sample as Comparison example | Aluminium chlorohydrate, cyclomethicone pentamer | — | 24 |
| 2 | Gilugel Sil5 | Cyclomethicone pentamer and Al-Mg-hydroxystearate | 25 | 25 |
| 3 | DC 345 | Cyclomethicone pentamer | 29 | 45 |
| 4 | Pro-myristyl 3 | PPG-3 myristyl ether | 5 | 5 |
| 5 | Ethanol | Ethanol | 1 | 1 |

The components 2, 3, 4 and 5 are mixed and homogenised. Component 1 is then stirred in.

The formulation A shows a better stability with regard to sedimentation on storage than formulation B does.

| | | | C | D |
|---|---|---|---|---|
| | \multicolumn{4}{c}{Antiperspirant aerosol formulation (master batch)} |
| | Components | INCI designation | \multicolumn{2}{c}{Proportion by weight (%)} |
| 1a | Activated aluminium chlorohydrate powder | Aluminium chlorohydrate | 33 | — |
| 1b | Sample as Example 3 | Aluminium chlorohydrate, cyclomethicone pentamer | — | 55 |
| 2 | Gilugel Sil5 | Cyclomethicone pentamer and Al-Mg-hydroxystearate | 29 | 29 |
| 3 | DC 345 | Cyclomethicone pentamer | 26 | 4 |
| 4 | DC 200 | Dimethicone | 2 | 2 |
| 5 | Isopropyl myristate | Isopropyl myristate | 10 | 10 |

The components 2, 3, 4 and 5 are mixed and homogenised. Component 1 is subsequently stirred in. Formulation D shows better sedimentation stability on storage than formulation C. For filling into aerosols, 1 part by weight of the master batch formulation is mixed with 3 parts of the propellant gas (propane, butane, n-pentane).

What is claimed is:

1. A process for synthesis of finely divided antiperspirant suspensions, comprising:

providing an antiperspirant salt consisting essentially of an Al salt which is effective as an antiperspirant wherein the Al salt exhibits a baud III proportion of >30% in HPLC, and which is described by an empirical formula as follows:

$$Al(OH)_{(3-b)}X_b zH_2O,$$

where b=0.4 to 3, z<4, and X=halogen;

mixing the Al salt into a non-aqueous oil phase to provide a mixture; and subsequently grinding the mixture with a suitable milling device at a temperature below 80° C. to provide a suspension having a preselected fineness.

2. The process according to claim 1, further comprising mixing a buffer substance with the antiperspirant salt under anhydrous conditions.

3. The process according to claim 1, wherein the Al salt effective as an antiperspirant exhibits a band III proportion of >40% in HPLC.

4. The process according to claim 1, wherein the non-aqueous oil phase consists of a non-polar organic fluid which is not miscible with water and which is at least one substance selected from the group consisting of alkanes, isoalkanes, monofunctional alcohols, polyfunctional alcohols, fatty acid esters of monobasic and dibasic carboxylic acids with monofunctional and polyfunctional alcohols, polyoxyethylenes, polyoxypropylenes, polyalkoxyalte ethers of alcohols, and silicone oil constituents.

5. The process according claim 4, wherein the silicone oil constituents are at least one substance selected from the group consisting of cyclic silicones, open-chain silicones, and mixtures thereof.

6. The process according to claim 1, wherein grinding is carried out in a ball mill.

7. The process according to claim 1, wherein grinding provides a suspension having a preselected fineness of 95%<20 μm.

8. The process according to claim 1, wherein grinding provides a suspension having a fineness of 95%<10 μm.

9. The process according to claim 1, wherein grinding is carried out at a temperature below 60° C.

10. The process according to claim 9, wherein grinding is carried out at a temperature below 40° C.

11. The process according to claim 2, wherein the buffer substance is an amino acid.

12. The process according to claim 11, wherein the amino acid is glycine.

13. A perspiration-inhibiting cosmetic preparation, comprising:

as active ingredient, an antiperspirant suspension prepared by the process according to claim 1.

14. The process according to claim 11, wherein b=0.45 to 1.0, and wherein X=chlorine.

* * * * *